United States Patent [19]

McCabe et al.

[11] Patent Number: 4,530,834

[45] Date of Patent: Jul. 23, 1985

[54] PREPARATION OF AN ENTOMOPATHOGENIC FUNGAL INSECT CONTROL AGENT

[75] Inventors: Dennis McCabe, Madison, Wis.; Richard S. Soper, Ithaca, N.Y.

[73] Assignee: The United States of America as represented by the Secretary of Agriculture, Washington, D.C.

[21] Appl. No.: 419,637

[22] Filed: Sep. 17, 1982

[51] Int. Cl.³ .................. A01N 63/00; C12N 3/00; C12N 1/00; C12N 1/14
[52] U.S. Cl. .................................. 424/93; 435/242; 435/243; 435/254; 435/911
[58] Field of Search ............... 435/242, 243, 254, 911; 424/93, 195

[56] References Cited

U.S. PATENT DOCUMENTS

| | | | |
|---|---|---|---|
| 3,616,246 | 10/1971 | Cherry | 195/81 |
| 3,766,685 | 10/1973 | Nickerson | 47/37 |
| 4,021,306 | 5/1977 | Soper | 195/81 |
| 4,021,765 | 5/1977 | Soper | 195/81 |
| 4,212,947 | 7/1980 | Torev | 435/254 |
| 4,280,000 | 7/1981 | Kozak et al. | 435/242 |

Primary Examiner—Thomas G. Wiseman
Assistant Examiner—Robin Lyn Teskin
Attorney, Agent, or Firm—M. Howard Silverstein; William E. Scott; David G. McConnell

[57] ABSTRACT

Entomopathogenic fungi useful in the control of insects is prepared by culturing mycelia in a suitable medium, harvesting the growing mycelia, treating the mycelia with a protective agent, drying the treated mycelia and grinding and storing the dried product.

8 Claims, No Drawings

4,530,834

PREPARATION OF AN ENTOMOPATHOGENIC FUNGAL INSECT CONTROL AGENT

BACKGROUND OF THE INVENTION

1. Field of The Invention

This invention relates to the use of entomopathogenic fungi in insect control and, more particularly, to the harvesting and subsequent treatment of cultured mycelia.

2. Description of The Art

Heretofore it was thought that since the resting spore was responsible for long term survival of the fungi, it was the most durable stage to produce, formulate and apply for insect control. The major problem has been to develop suitable methods to break resting spore dormancy. The use of other states of the fungi was believed impractical since they could not be produced in any way which would allow storage. U.S. Pat. Nos. 4,021,306 and 4,026,765 disclose production and germination of Entomophthorales resting spores. As with past research, current investigations are focused on the resting spore stage probably because the delicate and ephemeral nature of the vegetative stages of the Entomophthorales is well-known and it was not thought that these fungal states could be processed and used as a basis for a mycoinsecticide.

SUMMARY OF THE INVENTION

An object of this invention is to provide an entomopathogenic fungal insect control agent.

Another object is to provide a means of controlling insect populations using entomopathogenic fungi.

Still another object is to provide a means of harvesting and treating cultured mycelia to produce a dehydrated product which, upon rehydration, forms conidiophores and discharges conidia.

According to this invention the above objects are accomplished by a process wherein a fermentation medium in which mycelia is being actively grown is harvested, treated with a protective agent and then dried, ground and stored.

DESCRIPTION OF THE INVENTION

The process of this invention, that is, the harvesting of Entomophthorales mycelia to retain viability, is a significant step toward commercialization of the production and use of these pathogens as mycoinsecticides. Prior to the development of this process it was possible to work with only those few species which would produce resting spores in fermentation and even then a long maturation time was usually required before the spores could be used. Furthermore, the use of other states of these fungi was believed impractical since they could not be produced in any way which would allow storage. This invention overcomes these problems and provides a process by which material can be manufactured within one week and stored for future use.

Although we have limited our investigation of the utility of the invention to the order Entomophthorales, there appears to be no reason why the invention would not be successful with other orders of fungi. For insect control the product of the process of the invention is formulated as a wettable powder and sprayed on plants.

Optimum growth of the fungus depends upon the particular species being produced, but the chosen species can be grown in any suitable commercially available media. The fungus is harvested while in the active growth phase, before nutritional deprivation begins.

In harvesting, the liquid medium is discarded and the mycelia resuspended and slurried in a volume of water. The slurry is then filtered on a vacuum apparatus to obtain a thin, moist, mycelial sheet. The mats are then treated with a chemical protectant to prevent excessive loss of viability during storage, placed on racks at room temperature (about 22° C., 20–40% relative humidity) and allowed to stand for 4 to 5 hrs. The mats are then incubated at 4° C., 95–98% relative humidity for 12–18 hrs. Following the cold incubation, the mats are dried at room temperature under forced draft, then powdered and stored.

The process of this invention preserves the ability of the mycelia to produce conidiophores. These conidiophores then produce conidia which become airborne. When these spores come into contact with a susceptible insect a germ tube is formed which penetrates the body wall. The ensuing disease causes the insect to die.

It is important that harvesting and subsequent dehydration of the mycelia for storage be done in a manner that preserves it in a state from which, upon rehydration, the conidia mature and are discharged. Therefore, following are the details of a procedure which we have used successfully.

1. The mycelia is harvested by filtering the fermentation medium on an 18-mesh screen and allowing it to drain for two minutes. The liquid medium is discarded. The mycelia is then suspended in an equal volume of water.

2. Using about 1 liter of suspension/ft$^2$ of filter, the water is removed by vacuum leaving a moist mycelial mat about 1 to 2 mm thick weighing approximately 100 g, moist weight.

3. The mat is removed from the filter and placed on a supporting rack.

4. The mat is then sprayed with 10% w/v aqueous solution of maltose, glucose, or similar protective agent to saturation, usually about 30 to 40 g absorbed/ft$^2$.

5. The sprayed mats are incubated at 22° to 26° C. and 20 to 40% relative humidity, for 4 to 5 hrs. A drying rate of about 5 to 7 gm/ft$^2$/hr. is used.

6. The racks are then transferred to an incubator having a temperature of about 4° C., a humidity of 95 to 100%, and rapid air circulation with a drying rate of about 2 g/ft$^2$/hr., for about 18 hrs.

7. The racks are removed from the 4° C. dryer and the mats dried rapidly, about 60 g/ft$^2$/hr., at an ambient room temperature of about 20°–26° C., using a fan to provide a rapid flow of air. The mats are dried to crispness in about 4 to 6 hours.

8. The dried mats are removed from the racks and ground through a 20-mesh screen.

9. The powder from step 8 is sealed in a container and frozen or stored at 4° C.

We claim:

1. A process for preparing dried mycelia for use as an insect control agent comprising culturing mycelia in a suitable medium, harvesting growing mycelia, treating said mycelia with a chemical protectant to prevent excessive loss of viability during storage, incubating the treated mycelia for about four to five hours at about 22° to 26° C. and about 20 to 40% relative humidity, drying the incubated mycelia at about 4° C. with rapid air circulation for about 18 hours, drying further the partially dried mycelia at ambient room temperature of about 20° to 26° C. with rapid air flow for about four to six hours and then grinding and storing the dried mycelia.

2. A process for preparing dried mycelia for use as an insect control agent comprising culturing mycelia in a suitable fermentation medium, harvesting the mycelia while it is in active growth phase by filtering the fermentation medium on a suitable mesh screen to obtain thin mycelial mats, treating the mats with a 10% w/v aqueous solution of maltose, glucose or similar agent to saturation, incubating the treated mats for about four to five hours at about 22° to 26° C. and about 20 to 40% relative humidity, drying the incubated mycelial mats at about 4° C. and a relative humidity of about 95 to 100% with rapid air circulation for about 18 hours, drying further the partially dried mats at ambient room temperature of about 20° to 26° C. with rapid air flow for about four to six hours at a drying rate of about 60 g/ft$^2$/hr and grinding the mycelia to a powder.

3. The process of claim 2 wherein the cultured mycelia is collected on an 18-mesh screen in mats about 1 to 2 mm thick.

4. The process of claim 3 wherein the cultured mycelia is derived from a fungus of the order Entomophthorales.

5. A method of controlling insect populations on plants comprising growing a culture of a fungus of the order Entomophtorales on a suitable fermentation medium, filtering the medium while the fungi are actively growing to obtain a thin mycelial mat, treating the mycelial mat by spraying it to saturation with a chemical protectant to prevent excessive loss of viability during storage, incubating the treated mat for about four to five hours at about 22° to 26° C. and about 20 to 40% relative humidity, drying the incubated mycelial mat at about 4° C. with rapid air circulation for about 18 hours, drying further the partially dried mycelia at ambient room temperature of about 20° to 26° C. with rapid air flow for about four to six hours, grinding the dried mycelial mat to a powder, formulating the dried mycelia as a wettable powder and spraying the wettable powder on plants.

6. The ground dried mycelial product produced by the process of claim 1.

7. Mycelia in stable, dry, powdered form, said mycelia having been prepared by culturing mycelia in a suitable medium, harvesting growing mycelia, treating said mycelia with a chemical protectant to prevent excessive loss of viability during storage, incubating the treated mycelia for about four to five hours at about 22° to 26° C. and about 20 to 40% relative humidity, drying the incubated mycelia at about 4° C. with rapid air circulation for about 18 hours, drying further the partially dried mycelia at ambient room temperature of about 20° to 26° C. with rapid air flow for about four to six hours and grinding the dried mycelia, said mycelia being wettable and useful as an insect control agent.

8. The mycelia of claim 7 prepared from the mycelia of a fungus of the order Entomophthorales.

* * * * *